United States Patent
Comelli et al.

(10) Patent No.: US 7,491,386 B2
(45) Date of Patent: *Feb. 17, 2009

(54) TREATMENT OF ACTINOMYCES NAESLUNDII-RELATED DISEASES WITH EXOGENOUS LACTIC BACTERIA STRAINS

(75) Inventors: Elena-Maria Comelli, Lausanne (CH); Bernhard Guggenheim, Erlenbach (CH); Jean-Richard Neeser, Savigny (CH); Francesca Stingele, St-Prex (CH); Pier Sandro Cocconcelli, Piacenza (IT)

(73) Assignee: Nestec S.A., Vevey (CH)

( * ) Notice: Subject to any disclaimer, the term of this patent is extended or adjusted under 35 U.S.C. 154(b) by 54 days.

This patent is subject to a terminal disclaimer.

(21) Appl. No.: 10/995,891

(22) Filed: Nov. 23, 2004

(65) Prior Publication Data
US 2005/0074416 A1    Apr. 7, 2005

Related U.S. Application Data

(63) Continuation of application No. 10/305,024, filed on Nov. 27, 2002, now abandoned, which is a continuation of application No. PCT/EP01/06268, filed on May 30, 2001, and a continuation of application No. 09/779,596, filed on Feb. 9, 2001, now Pat. No. 6,942,849, which is a continuation of application No. PCT/EP99/05473, filed on Jul. 26, 1999.

(30) Foreign Application Priority Data

Dec. 8, 1998 (EP) .................................. 98202707
Feb. 6, 2000 (EP) .................................. 00201948

(51) Int. Cl.
*A01N 63/00* (2006.01)
*C12N 1/20* (2006.01)
*C12P 1/00* (2006.01)

(52) U.S. Cl. ..................... 424/93.4; 424/93.45; 435/41; 435/243; 435/252.4; 435/252.9; 435/253.4; 435/822; 435/885

(58) Field of Classification Search .................. None
See application file for complete search history.

(56) References Cited

U.S. PATENT DOCUMENTS

| | | | |
|---|---|---|---|
| 4,992,420 A | 2/1991 | Neeser | 514/8 |
| 5,032,399 A | 7/1991 | Gorbach et al. | 424/93 |
| 5,135,739 A | 8/1992 | Tsurumizu et al. | 424/50 |
| 5,358,858 A | 10/1994 | Chiang et al. | 435/71.1 |
| 5,368,845 A | 11/1994 | Gaffar et al. | 424/54 |
| 5,427,767 A | 6/1995 | Kresse et al. | 424/93.2 |
| 5,427,769 A | 6/1995 | Berrocal et al. | 424/54 |
| 5,494,664 A | 2/1996 | Brassart et al. | 424/93.4 |
| 5,503,865 A | 4/1996 | Behringer et al. | 426/587 |
| 5,756,665 A | 5/1998 | Mollet et al. | 530/326 |
| 5,833,953 A | 11/1998 | Berrocal et al. | 424/49 |
| 5,955,602 A | 9/1999 | Favre et al. | 536/123 |
| 6,036,952 A | 3/2000 | Oh | 424/93.1 |
| 6,635,238 B2 * | 10/2003 | Delisle | 424/49 |
| 2004/0029171 A1 * | 2/2004 | Wagner et al. | 435/7.1 |

FOREIGN PATENT DOCUMENTS

| | | |
|---|---|---|
| EP | 0 524 732 A2 | 1/1993 |
| EP | 0 699 689 A1 | 3/1996 |
| EP | 0 759 469 | 2/1997 |
| JP | 59220191 | 12/1984 |
| JP | 4021633 A | 1/1992 |
| JP | 05004927 | 1/1993 |
| JP | 08256681 | 10/1996 |
| JP | 09084521 | 3/1997 |
| WO | WO 92/1 4475 | 9/1992 |
| WO | WO94/12150 | 6/1994 |

OTHER PUBLICATIONS

Ahmady K. et al., "Distribution of Streptococcus mutans and Streptococcus sobrinus at Sub-Sites in Human Approximal Dental Plague," Caries Res. 27:135-139 (1993).
Bentley R. W. et al., "Intrageneric Structure of Streptococcus Based on Comparative Analysis of SmallSubunit rRNA Sequences," International Journal of Systematic Bacteriology, 487-494 (1991).
Boumerdassi, H. et al., "Isolation and Properties of *Lactococcus lactis* subsp. *lactis* biovar diacetylactis CNRZ 483 Mutants Producing Diacetyl and Acetoin from Glucose," Applied and Environmental Microbiology, 2293-2299 (1997).
Busscher et al., "Streptococcus thermophilus and Its Biosurfactants Inhibit Adhesion by Candida spp. on Silicone Rubber," Applied and Environmental Microbiology 63(10):3810-3817 (Oct. 1997).
Frandsen E. V.G. et al., "Ecology of Viridans Streptococci in the Oral Cavity and Pharynx," Oral Microbiol. Immunot. 6:129-133 (1991).
Fujisawa T, et al., "Taxonomic Study of the *Lactobacillus acidophilus* Group with Recognition of *Lactobacillus gallinarum* sp. nov. and *Lactobacillus johnsonii* sp. no. and Synonymy of *Lactobacillus acidophilus* Group A3 (Johnson et al. 1980) with the Type Strain of *Lactobacilus amylovorus*," International Journal of Systematic Bacteriology, 487-491 (1992).
Gibbons R.J. et al., "Strains of Streptococcus mutans and Streptococcus sobrinus Attach to Different Pellicle Receptors," Infection and Immunity, 555-561 (1986).
Gmür, R. and Guggenheim, B., "Antigenic heterogeneity of Bacteroides intermedius as recognized by monoclonal antibodies," Infect. Immun. 42, 459-470 (1983).
Gonzalez, B., et al., "Detection, purification, and partial characterization of plantaricin C, a bacteriocin produced by a *Lactobacillus plantarum* strain of dairy origin," Appl. Environ. Microbiol. 60:2158-2163 (1994).
Granato D.A. et al., "A mouse monoclonal IgE antibody anti bovine milk β-lactoglobutin allows studies of allergy in the gastrointestinal tract," Clin. exp. Immunol. 63:703-710 (1986).

(Continued)

*Primary Examiner*—David M. Naff
*Assistant Examiner*—Deborah K. Ware
(74) *Attorney, Agent, or Firm*—Bell, Boyd & Lloyd LLP

(57) ABSTRACT

A lactic bacteria strain that is exogenous to the oral microflora is selected for its ability to adhere the pellicle of the teeth and to produce a growth inhibition factor. This strain is used for the preparation of a composition intended for reducing dental plaque and for treating or preventing root caries and other diseases related to *Actinomyces naeslundii* in mammals.

17 Claims, 2 Drawing Sheets

OTHER PUBLICATIONS

Hiroi T. et al., "De nova gtucan synthesis by mutans streptococcal glucosyltransferases present in pellicle promotes firm binding of Streptococcus gordonii tooth surfaces," FEMS Microbiology letters 96:193-198 (1992).

Ito Y. et al., "Cloning and Nucleotide Sequencing of I-Lactate Dehydrogenase Gene from Streptococcus thermophilus M-192," Biosci. Biotech. Biochem. 58:1569-1573 (1994).

Kolenbrander P.E., "Coaggregations among Oral Bacteria," Methods in Enzymology 253:385-397 (1995).

Lindquist B. et al., "Dental Location of Streptococcus mutans and Streptococcus sobrinus in Humans Harboring Both Species," Caries Res. 25:146-152 (1991).

Lindquist B. et al., "Distribution and Prevalence of Mutans Streptococci in the Human Dentition," J. Dent Res. 69(5):1160-1166 (1990).

Loesche, W.J., et al., "The Predominant Cultivable Flora of Tooth Surface Plaque Removed from Institutionalized Subjects," Arch. Oral Biol. 17, 1311-1325 (1972).

Meurman J.H. et al., "Recovery of Lactobacillus Strain GG (ATCC 53103) from Saliva of Healthy Volunteers after Consumption of Yoghurt Prepared with the Bacterium," *Microbial Ecology in Health and Disease* 7:295-298 (1994).

Perdigon G. et al., Systemic augmentation of the immune response in mice by feeding fermented milks with *Lactobacillus casei and Lactobacillus acidophilus*, Immunology 63:17-23 (1988).

Perdigon G. et al., "Actividad Immunopotenciadora De Bacterias Lacticas Adminitradas Por Via Oral," Medicina 46:751-754 (1986).

Platteeuw C. et al., "Metabolic Engineering of *Lactococcus lactis*: Influence of the Overproduction of α-Acetotactate Synthase in Strains Deficient in Lactate Dehydrogenase as a Function of Culture Conditions," Applied and Environmental Microbiology 61(11):3967-3971, (1995).

Schüpbach P. et al., "Incorporation of Caseinoglycomacropeptide and Caseinophosphopeptide into the Salivary Pellicte Inhibits Adherence of Mutans Streptococci," J. Dent Res 75(10):1779-1788 (1996).

Skopek R.J. et al., "The influence of saliva on interbacterial adherence," Oral Microbiol Immunol 9:19-24 (1994).

Tanzer J.M. et al.,"Competitive Displacement of Mutans Streptococci and Inhibition of Tooth Decay by Streptococcus salivarius TOVE-R," Infection and Immunity, 44-50 (1985).

Van Hoogmoed et al., "The role of biosurfactants in affecting initial microbial adhesion mechanisms," Biofilms: Recent Advances in Their Study and Control 237-251 (Evans, L. V. ed.) (Hardwood Academic Publishers, Amsterdam 2000).

\* cited by examiner

TREATMENT OF ACTINOMYCES NAESLUNDII-RELATED DISEASES WITH EXOGENOUS LACTIC BACTERIA STRAINS

CROSS-REFERENCE TO RELATED APPLICATIONS

This application is a continuation of abandoned U.S. application Ser. No. 10/305,024 filed Nov. 27, 2002, which is a continuation of International Application No. PCT/EP01/06268, filed May 30, 2001; and a continuation of U.S. application Ser. No. 09/779,596, now U.S. Pat. No. 6,942,849, issued on Sep. 13, 2005, which is a continuation of International Application No. PCT/EP99/05473, filed Jul. 26, 1999, the disclosures of all of which are expressly incorporated herein by reference thereto.

TECHNICAL FIELD

The present invention relates to the incorporation in the oral microflora of exogenous lactic bacteria that are able to modulate the colonization of *A. naeslundii* and to reduce the severity of *A. naeslundii*-related diseases.

BACKGROUND ART

The mouth (oral cavity) contains a resident and a non-resident microflora. The first includes microorganisms that are able to establish a more or less permanent residence on the oral surfaces. These bacteria are mainly localised on the tongue, the buccal mucosa and the teeth while the gingiva, lips, cheeks, palate and floor of the mouth only support a very sparse microflora.

The dental plaque is a film that forms on the surface of teeth consisting of bacterial cells in a matrix of extracellular polysaccharides and salivary products. Immediately after eruption, the teeth are covered with an amorphous layer of saliva, the acquired enamel pellicle (AEP) that is about 1.3 μm thick and cannot be removed by normal tooth brushing. The deposition of bacteria on teeth follows immediately the formation of the AEP and plaque becomes evident in 8-12 hours as a multi-layered structure. The first layer consists of bacteria (earliest colonisers) that attach to teeth mainly via specific adhesion-receptor recognition; it forms a substratum for the second colonisers that adhere one to the other via analogous specific binding or via simple juxtaposition. Plaque cohesion is essentially guaranteed by three mechanisms: the presence of a salivary pellicle on the outer bacteria layer, the specific co-aggregation among the different bacterial species, and the glucans synthesized by the bacteria that remain entrapped in the plaque matrix (Skopek et al., Oral Microbiol. Immunol., 2, 19-24, 1994; Kolenbrander et al., Meth. Enzymol., 253, 385-397, 1995; Hiroi et al., FEMS Microbiol Lett., 96, 193-198, 1992; Gibbons et al., Infect. Immun., 52555-561, 1986).

On the tongue and the buccal mucosa, the natural resident microflora includes microorganisms selected from *Streptococcus, Veillonella, Bacteroides* and *Haemophilus*. On the teeth, Streptococci and *Actinomyces* predominate but a variety of Gram positive and negative cocci and rods can be found.

For example, Frandsen et al. showed that *S. sanguis* predominates on the buccal mucosa but its primary habitat is the surface of teeth, that *S. gordonji* grows in the mature supragingival plaque, and that *S. oralis* and *S. mitis* grow in the initial dental plaque (Oral Microbiol. Immunol., 6, 129-133, 1991). Strains belonging to the mutans group are localized on teeth (*S. criscetus, S. downei, S. ferus, S. macacae, S. mutans, S. rattus, S. sobrinus*). Strains belonging to the *S. milleri* group predominate in dental abscesses (*S. anginosus, S. constellatus, S. intermedius*) (Bentley et al., Int. J. System. Bacter. 1991, 41, 487-494; Wood et al., The Genera of Lactic Acid Bacteria, Blackie Academic and Professional, Chapman & Hall, W. H. eds., 1995).

Many of these microorganisms are innocuous commensally, but a lot of them have been recognized as the etiologic agent of quite a few diseases (Hill, M. J. and Marsh, P. D. eds. Human Microbial Ecology, 1990, CRC Press, Boca Raton Fla., USA).

In particular, *Actinomyces naeslundii* genospecies 1 (formerly *A. naeslundii*) and 2 (formerly *A. viscosus*) are common members of human dental plaque. They are among the strongest plaque forming oral strains, because of their capacity to firmly adhere to the teeth and to coaggregate with many other bacterial species, thus fostering their establishment in the mouth. Moreover, in the elderly, they are commonly isolated at root caries sites, and they are believed to be the major etiological agent of this disease (Bowden, G. H., et al. 1999, The diversity and distribution of the predominant ribotypes of *Actinomyces naeslundii* genospecies 1 and 2 in samples from enamel and from healthy and carious root surfaces of teeth. *J. Dent. Res.* 78, 1800-1809).

The organic acids produced by oral bacteria during the fermentation process directly cause dental caries. These acids attack the hard tissue of teeth with the consequent release of ions such as calcium, phosphate, carbonate, magnesium, fluoride, and sodium. When the pH in the oral cavity again increases to around neutrality, the saliva becomes saturated with calcium so that calcium liberation from the tooth is prevented. Among all the food residues found in the mouth, carbohydrates show the highest caries promoting effect since they are directly available for fermentation by oral bacteria.

Potentially all microorganisms that ferment sugars are cariogenic, but the primary etiological agents of coronal and root caries are the mutans streptococci because they are strong acid producers; *Lactobacilli*, that are highly aciduric, however, can also be implicated. In humans, *S. mutans* and *S. sobrinus* are the more cariogenic strains, and live on teeth while not colonizing the entire dentition. Their number is also less on anterior teeth than on molar teeth (Lindquist et al., Dent. Res., 69, 1160-1166, 1990). Moreover in human approximal plaque, *S. mutans* and *S. sobrinus* preferentially colonize the most caries-prone site apical to the contact area (Ahmady et al., Caries Res., 27, 135-139, 1993). A higher prevalence of *S. sobrinus* was also found in the molar regions compared with that of *S. mutans* (Lindquist et al., Caries Res., 25, 146-152, 1991).

*S. mutans* and *S. sobrinus* have been shown to attach to the pellicle of teeth mainly via specific adhesion-receptor interaction. Gibbons et al. showed that *S. mutans* carries an adhesion which binds to salivary components in the pellicle, while *S. sobrinus* cells appear to possess an adhesion which binds to glucan in the pellicle (Infect. human., 52, 555-561, 1986).

The transient microflora comprises exogenous bacteria that can be occasionally present in the mouth, but that do not establish a permanent residence (even if repeated oral administrations of these bacteria are carried out). All the food bacteria, and in particular lactic acid bacteria, can be part of this transient microflora.

These exogenous lactic bacteria have never been shown to be capable of directly adhering to the pellicle of teeth. Repeated administration of exogenous lactic bacteria may lead to colonization of the mouth on all the oral surfaces, such as the tongue, the buccal mucosa, the gingiva, lips, cheeks, palate, floor, and the teeth. This colonization may result from attachments via specific bindings to bacteria of the resident microflora (co-aggregation phenomena), via entrapment in the matrix of polysaccharide produced by the resident bacteria, or via adhesion to saliva proteins (especially glycoproteins).

*Lactobacillus casei rhamnosus* GG (ATCC53103) has been reported to colonize the mouth, most probably on the epithelium of the buccal mucosa. This strain also adheres to the epithelium of the intestinal tract (U.S. Pat. No. 5,032,399, Gorbach et al.; Micr. Ecol. In Health and Dis., 2, 295-298, 1994). By contrast *L. rhamnosus* does not adhere to teeth.

Japanese patent no. 4021633 (Cyconmedix KK) also reported colonization of the mouth by *Lactobacillus acidophilus*, most probably on the epithelium of the buccal mucosa. Many *Lactobacillus acidophilus* are known to also adhere to the epithelium of the intestinal tract (EP577904; EP199535; Perdigon et al., Medicina, 46, 751-754, 1986; Perdigon et al., Immunology, 63, 17-23, 1988).

Exogenous bacteria can also produce factors that inhibit the growth of the resident microflora in the mouth. For example, EP759469 (Sociétédes Produits Nestlé) described the use of a bacteriocin produced by *Micrococcus varians* for inhibiting the development of the oral pathogens *S. sobrinus, S. sanguis, S. mutans* and *A. viscosus*.

There are several strategies to minimize the development of resident microflora of the mouth. For example, by administering commensal bacteria of the resident microflora that are not cariogenic, such as *Streptococcus salivarius* and/or *Stomatococcus mucilaginosus*, and/or repeated administration of exogenous lactic bacteria such as *L. casei, L. fermentum, L. acidophilus, L. crispatus, L. gasseri, L. salivarius, L bulgaricus*, and *S. salivarius* (Tanzer et al., Infec. and Immunity, 48, 44-50, 1985; WO92/14475).

The application of bacteriocins is also one of the investigated strategies that have been set up to reduce tooth caries. These molecules have attracted interest as prospective anti-caries agents and as factors important in modulating colonization of the oral cavity. The anti-carie potential of applying bacteriocins comes from their potent and broad antibacterial activity against mutans streptococci and bacteria associated with dental plaque and their natural occurrence in bacteria regarded as being safe to humans (U.S. Pat. No. 5,368,845 to Colgate, and WO 94/12150 to Smithkline Beecham).

The application of milk derivatives is also of interest for the health of the mouth. Indeed, U.S. Pat. No. 5,427,769 (Nestec S. A.) describes another alternative wherein dental caries are prevented by contacting teeth with an edible composition containing micellar casein in amount sufficient to inhibit colonization by *Streptococcus sobrinus*. EP748591 (Societe des Produits Nestle S. A.) also reports the use of fluoridated micellar casein or its micellar subunits for treating dental caries or plaque. U.S. Pat. No. 4,992,420 (Nestec S. A.) describes treatment of the buccal cavity with kappa-caseinoglycomacropeptide derived from milk for eradicating plaque and caries.

Lactic bacteria that are not part of the resident microflora of the mouth have never been shown to be really capable of directly adhering to the pellicle of teeth. By colonizing the surface of teeth, however, such lactic bacteria could exert an inhibitory activity against the growth of the resident microflora, including oral pathogens.

It is to note that the prior art does not provide any information concerning strains that can establish in the oral cavity by directly adhering to the pellicle of the teeth and also produce factors such as growth inhibition factors, which can modulate the colonization of *A. naeslundii* so as to reduce the severity of *A. naeslundii*-related diseases.

SUMMARY OF THE INVENTION

The present invention aims to provide the use of lactic bacteria that are exogenous to the oral microflora, which have been selected for their ability to adhere to the tooth surface and to produce a *Actinomyces naeslundii* growth inhibition factor, and the preparation of a composition intended for reducing dental plaque and for treating or preventing root caries or other diseases or infections related to or caused by *Actinomyces naeslundii* in mammals.

The lactic bacteria may be selected from the group consisting of *Streptococcus thermophilis, Lactococcus lactis* subsp. *lactis*, and *Lactococcus lactis* subsp. *lactis biovar diacetylactis* and particularly from the group consisting of the strains CNCM I-1984, CNCM I-1985, CNCM I-1986, and CNCM I-1987. The lactic bacteria strain may be of dairy origin.

Thus, by colonizing the surface of teeth and producing growth inhibition factors, such lactic bacteria can exert a significant reduction of the extent of *Actinomyces naeslundii*, thus reducing dental plaque, root caries and other *Actinomyces naeslundii* related diseases and infections.

The lactic bacteria strain may be administered in an edible composition, and the composition may contain at least $10^4$-$10^9$ cfu/g of the lactic bacteria strain. The lactic bacteria may be administered in combination with a bacteriocin.

Another object is to provide a composition for maintaining the health of the mouth by reducing the colonization of *Actinomyces naeslundii*, said composition comprises an exogenous lactic bacteria that has been selected for its ability to adhere to the tooth surface and to produce a growth inhibition factor.

Such a composition may contain at least $10^4$-$10^9$ cfu/g of lactic bacteria.

The present invention also relates to a composition for maintaining mammal mouth health by reducing *Actinomyces naeslundii* colonization therein. The composition comprises at least one lactic bacteria strain that is exogenous to oral microflora, where the strain is selected for its ability to adhere to teeth pellicle and to produce a growth inhibition factor and is present in an amount sufficient to reduce or inhibit the colonization of *Actinomyces naeslundii*.

The invention also provides a method of preventing or treating *Actinomyces naeslundii* related infections, particularly dental plaque extent and root caries in mammals. *Actinomyces naeslundii* related diseases may be prevented or treated in mammals according to the present invention by administering to a mammal a composition containing at least one lactic bacteria strain selected for its ability to adhere to the tooth surface and to produce a *Actinomyces naeslundii* growth inhibition factor in an amount sufficient to reduce or inhibit the colonization of *Actinomyces naeslundii*. Further, such lactic bacteria strain may be provided in a dentifrice composition for maintaining mammal mouth health.

DETAILED DESCRIPTION OF THE PREFERRED EMBODIMENTS

Figure 1A:
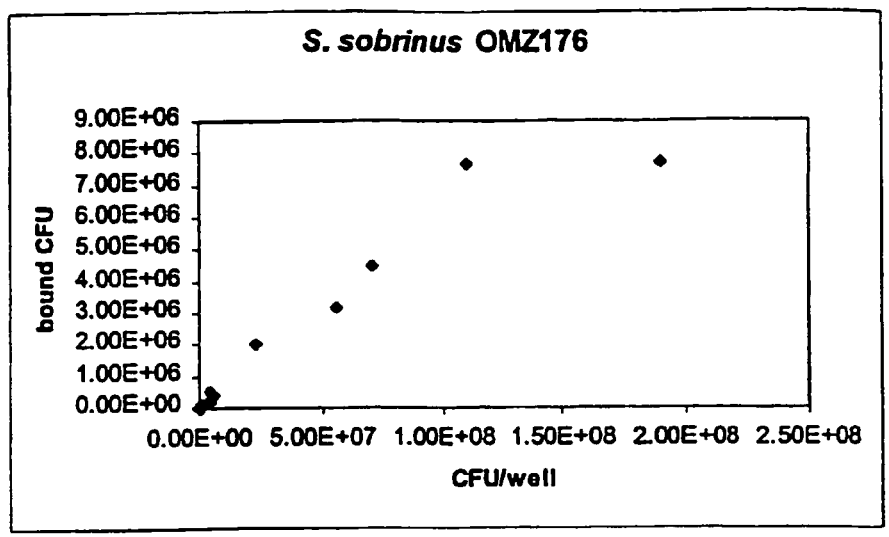
FIG. 1 represents the adhesion saturation curves for *S. sobrinus* OMZ 176 (1a), *L. lactis* NCC2211 (1b), and *S. thermophilus* NCC1561 (1c)

Within the following description, the mouth defines the oral cavity of humans or animals such as pets, composed by the oral mucosa (gums, lips, cheeks, palate and floor of the mouth), the tongue and the teeth (including artificial structures).

The terms "inhibition growth factor" defines any extracellular substance produced by the adherent exogenous lactic bacteria that enables it to inhibit the growth of *A. naeslundii*.

Resident microflora of the mouth includes all microorganisms that naturally live in the mouth because they can establish a permanent residence on the oral surfaces. The resident microflora of the mouth also includes bacteria that live in the interfacial region between the dental hard and soft tissues (the junction tooth-gingiva), even thought the gingival crevice and the periodontal pocket are not present in a healthy mouth. This microflora includes microorganisms selected from *Streptococcus, Staphylococcus, Enterococcus, Micrococcus, Peptostreptococcus, Peptococcus, Lactobacillus, Corynebacterium, Actinomyces, Arachnia, Rothia, Alcaligenes, Eubacterium, Propionibacterium, Bifidobacterium, Bacillus, Clostridium, Neisseria/Branhamella, Veillonella*, Enterobacteriaceae, *Campylobacter, Eikenella, Actinobacillus, Capnocytophga, Haemophilus, Simonsiella, Bacteroides, Fusobacterium, Porphyromonas, Prevotella, Leptotrichia, Wohlinella/Selenomonas, Mycoplasma, Candida, Spirochaetes, Protozoa*.

Transient microflora comprises exogenous bacteria that can be occasionally present in the mouth, but that do not establish a permanent residence. This transient microflora may comprise all the food micro-organisms, such as the bifidobacteria (*B. infantis, B. adolescentis, B. breve* and *B. longum*); the lactococci (*Lactococcus lactis* subsp. *lactis*, *Lactococcus lactis* subsp. *cremoris*, and *Lactococcus lactis* subsp. *lactic biovar diacetylactis*); the streptococci (*Streptococcus thermophilus, S. lactis, S. lactis cremoris* and *S. lactis diacetylactis*); the Lactobacilli (*Lactobacillus delbrueckii* subsp. *bulgaricus, Lactobacillus helveticus, Lactobacillus farciminis, Lactobacillus alimentarius, Lactobacillus casei* subsp. *casei, Lactobacillus delbruckii* subsp. *lactis, Lactobacillus sake, Lactobacillus curvatus, Lactobacillus fermentum*; and the acidophile group comprising *L. johnsonii*; (see Fujisawa et al., Int. J. Syst. Bact., 42, 487-491, 1992); the pediococci (*Pediococcus pentosaceus, Pediococcus acidilactici*, and *Pediococcus halophilus*); the enterococci; the staphilococci (*Staphylococcus xylosus* and *Staphylococcus carnosus*); the micrococci (*Micrococcus varians*); yeast of the genus *Debaromyces, Candida, Pichia, Torulopsis* and *Saccharomyces*; and mold of the genus *Aspergillus, Rhizopus, Mucor* and *Penicillium*.

The object of the present invention is to use lactic bacteria that are not part of the resident microflora of the mouth, that is lactic bacteria that are low acidifying and that are capable of adhering directly to the pellicle of the teeth, to prepare a composition intended for the prophylaxis or the treatment of dental caries, dental plaque, and periodontal infection.

In one embodiment of the invention the lactic bacteria have been genetically modified to increase its adherence to the pellicle of the teeth via adhesion factors and/or genetically modified to be even less acidifying, contributing to a pH in the oral cavity of about 5.5 to 7.

The lactic bacteria may be selected from the group consisting of:

an acidifying lactic bacteria that adheres to the pellicle of the teeth and that has been genetically modified so that it is low acidifying compared to resident microflora;

a non adherent lactic bacteria that is low acidifying and that has been genetically modified so that it adheres to the pellicle of the teeth;

a non-adherent acidifying lactic bacteria that has been genetically modified so that it adheres to the pellicle of the teeth and genetically modified so that it is low acidifying compared to resident microflora.

In another embodiment the bacteria, that is not part of the resident microflora, is low acidifying compared to resident microflora and is capable of adhering directly to the pellicle of the teeth.

In another embodiment the composition for the health of the mouth comprises (1) at least a lactic bacteria that is not part of the resident microflora of the mouth, which is capable of adhering directly to the pellicle of the teeth and contributing to a pH in the oral cavity of above 5.5, and (2) any form of caseinoglycomacropeptide, micellar casein, fluorinated micellar casein, renneted milk, or bacteriocin.

The invention also provides a method for screening lactic bacteria capable of adhering to tooth. The method comprises the steps of: (1) preparing monoclonal antibody recognizing specific surface proteins of a lactic bacteria strain capable of adhering to the teeth, and (2) screening any lactic bacteria strain by use of the monoclonal antibody of strain capable of adhering to the teeth.

The lactic bacteria according to the invention that are low acidifying and capable of adhering directly to the pellicle of the teeth that are used to prepare compositions for the prophylaxis or the treatment of dental caries, dental plaque, and periodontal infection displace pathogenic bacteria from the teeth or prevent the attachment of the pathogenic bacteria. The lactic bacteria according to the invention are "low acidifying," which means that they are less acidifying than pathogenic strains. Accordingly, they contribute to a pH in the oral cavity of about 5.5 to 7. Preferably, they are from dairy origin.

The lactic bacteria according to the invention adhere to the pellicle of the teeth via specific or unspecific interactions and/or adhesion factors. The specific adhesion factors are proteins or polysaccharides.

At least one lactic bacteria is selected from the group consisting of *Streptococcus thermophilus, Lactococcus lactis* subsp. *lactis*, and *Lactococcus lactis* subsp. *Lactis biovar diacetylactis* and particularly from the group consisting of the strains CNCM 1-1984, CNCM 1-1985, CNCM 1-1986, CNCM 1-1987, and LMG P-18997. These strains have been selected among lactic bacteria strains for their capacity to adhere to the pellicle of the teeth and their optimal growth temperature of about 37° C., which is the temperature in the oral cavity. Moreover they are capable of fermenting glucose and sucrose and do not synthesize glucans, which are factors leading to the pathogenicity of the cariogenic strains.

In one embodiment of the invention the lactic bacteria are genetically modifying so that they adhere to the pellicle of the teeth via adhesion factors. For lactic bacteria that already adhere to the pellicle of the teeth, this modification makes the strains more adherent to the surface of the teeth. In the same way, any non-adherent lactic acid bacteria (not *Lactobacilli*) can be genetically modified so that it adheres to the pellicle of the teeth. This modification of the lactic bacteria can be achieved, for example, by insertion of the genes X17390, X14490 or X53657 (GenBank accession numbers). These gene are responsible in *S. mutans* for the expression of the Antigen I/II that mediates adhesion to salivary glycoproteins.

According to the invention, it is also possible to genetically modify lactic bacteria so that they are low acidifying. For lactic bacteria that is already low acidifying this modification increases the effect by further decreasing lactic acid production. This modification can be achieved in many ways. Preferably, the modification is achieved according to one the protocols described in the following documents: Boumerdassi et al., Appl. Environ. Microbiol., 63, 2293-2299, 1997; Plattecuw et al., Appl. Environ. Microbiol, 61, 3967-3971, 1995; Ito et al., Biosci. Biotechnol. Biochem., 58, 1569-1573, 1994.

With respect to one object of the present invention, the use of an exogenous lactic bacteria that has been selected for its ability to adhere to the tooth surface and to produce a growth inhibition factor, for the preparation of a composition intended for reducing dental plaque and for treating or preventing root caries or other disease related to *Actinomyces naeslundii*, is concerned.

The lactic bacteria may be selected from the group consisting of *Streptococcus thermophilus*, *Lactococcus lactis* subsp. *lactis*, and *Lactococcus lactis* subsp. *lactis* biovar *diacetylactis* and particularly from the group consisting of the strains *Streptococcus thermophilus* (NCC 1529) (CNCM I-1984), *Streptococcus thermophilus* (NCC 1561) (CNCM I-1985), *Lactococcus lactis* subsp. *lactis* (NCC 2211) (CNCM I-1986), *Lactococcus lactis* subsp. *lactis* biovar *dioacetylactis* (NCC 2225) (CNCM I-1987).

The lactic bacteria are preferably of dairy origin (i.e. originating from milk or cheese, for example).

The lactic bacteria according to the invention is "low acidifying", which means that it is less acidifying than pathogenic strains. Accordingly, it can contribute to a pH in the oral cavity of about 5.5-7.

These strains have been selected among lactic bacteria strains for their capacity of adherence to the pellicle of the teeth, and their optimal growth temperature is about 37° C., which is the temperature in the oral cavity. They are also capable of producing a growth inhibition factor, which combined to their adhesion properties allow them to significantly decrease the colonization extent of *A. naeslundii* genospecies 1 and 2.

Moreover they are capable of fermenting glucose and sucrose and do not synthesize glucans, which are factors of pathogenicity of the cariogenic strains.

It is also possible to use at least one lactic bacteria strain in combination with a bacteriocin, for example.

According to the invention, at least one lactic bacteria, genetically modified or not, is used in an "effective amount" for the preparation of compositions intended for the prophylaxis or the treatment of dental caries, dental plaque, and periodontal infection in humans or animals such as pets. This quantity is preferably between $10^4$-$10^9$ cfu/g.

It is also possible to use the at least one lactic bacteria, in combination with milk derivatives, such as milk, fermented milk, or milk derivatives selected from any forms of caseinoglycomacropeptide, micellar casein, fluorinated micellar casein, renneted milk, or bacteriocin, for example.

The exogenous lactic bacteria may be used in an amount of at least $10^4$-$10^9$ cfu/g of lactic bacteria.

The effect of incorporating the above-mentioned bacteria in the oral microflora was tested in a rat model. The strains CNCM I-1985 and CNCM-1986 were able to modulate the oral microbial ecology, significantly reducing the number of total CFU. More specifically, the strains were able to significantly decrease the colonization extent of *A. naeslundii* genospecies 2, with which the rats had been infected (see examples).

Biochemical Characterization of the Selected Strains

Fermentation patterns: 49 simple sugars were tested with the api 50 CH bioMerieux strip test (bioMérieux SA, 69280 Marcy-l'Etoile, France) and the results are given in Table 1.

Acidification curves: Acidification curves were determined at 37° C. under the following conditions:

*S. sobrinus* OMZ 176: FUM sucrose 1% and FUM glucose 1%

*S. thermophilus* CNCM 1-1985: Belliker sucrose 1% and Belliker glucose 1% Inoculation was always 5%. The pH was recorded every 20 min.

*S. thermophilus* CNCM 1-1985, from sucrose fermentation, lowers the pH to 4.5, while *S. sobrinus* OMZ 176 lowers the pH to 4.

TABLE 1

Sugar fermentation of *L. lactis* CNCM I-1987, *L. lactis* CNCM I-1986, *S. thermophilus* CNCM I-1984, *S. thermophilus* CNCM I-1985, and *S. thermophilus* LMG P-18997.

| Sugar | *L. lactis* CNCM I-1987 | *L. lactis* CNCM I-1986 | *S. th.* CNCM I-1984 | *S. th.* CNCM I-1985 | *S. th.* LMG P-18997 |
|---|---|---|---|---|---|
| Adonitol | +++ | | | | |
| Aesculin | ++ | +++ | | | |
| Amygdalin | ++++ | | | | |
| D-Arabinose | | | | | |
| L-Arabinose | | | | | |
| D-Arabitol | | | | | |
| L-Arabitol | +++ | | | | |
| Arbutin | +++ | +++ | | | |
| Cellobiose | +++ | +++ | | | |
| Dulcitol | | | | | |
| Erythritol | | | | | |
| D-Fructose | + | ++++ | | | |
| D-Fucose | | | | | |
| L-Fucose | | | | | |
| Galactose | ++ | ++++ | | | |
| β-Gentiobiose | | +++ | | | |
| Gluconate | | | | | |
| 2-ketoGluconate | | | | | |
| 5-ketoGluconate | | | | | |
| GlcNAc | + | ++++ | | | |
| D-Glucose | + | ++++ | + | ++ | ++ |
| Glycerol | | | | | |
| Glycogen | | | | | |
| Inositol | | | | | |
| Inulin | | | | | |
| Lactose | + | ++++ | +++ | ++++ | ++++ |
| D-Lyxose | | | | | |
| Maltose | ++ | | | | |
| Mannitol | +++ | ++ | | | |
| D-Mannose | + | ++++ | | | |
| Melezitose | | | | | |
| Melibiose | | | | | |
| α-Methyl-D-glucoside | | | | | |
| α-Methyl-D-mannoside | | | | | |
| D-Raffinose | | | | | |
| Rhamnose | | | | | |
| Ribose | ++ | ++ | | | |
| Salicin | +++ | +++ | | | |
| Sorbitol | | | | | |
| L-Sorbose | | | | | |
| Starch | | | | | |
| Sucrose | | | +++ | ++++ | +++ |
| D-Tagatose | | | | | |

TABLE 1-continued

Sugar fermentation of *L. lactis* CNCM I-1987, *L. lactis* CNCM I-1986, *S. thermophilus* CNCM I-1984, *S. thermophilus* CNCM I-1985, and *S. thermophilus* LMG P-18997.

| Sugar | L. lactis CNCM I-1987 | L. lactis CNCM I-1986 | S. th. CNCM I-1984 | S. th. CNCM I-1985 | S. th. LMG P-18997 |
|---|---|---|---|---|---|
| Trehalose | ++ | | | | |
| D-Turanose | ++ | | | | |
| Xylitol | +++ | | | | |
| D-Xylose | | | | | |
| L-Xylose | | | | | |
| β-methyl-xyloside | | | | | |

+, ++, +++, ++++ show if the fermentation begins after 3, 6, 24 or 48 hours.

The strains *Sreptococcus thermophilus* (NCC 1529), *Sreptococcus thermophilus* (NCC 1561), *Lactococcus lactis* subsp. *lactis* (NCC 2211), *Lactococcus lactis* subsp. *lactis biovar dioaetylactis* (NCC 2225) were deposited under the Budapest Treaty, at the Collection Nationale de Culture de Microorganismes (CNCM I-1984, CNCM I-1985, CNCM I-1986 and CNCM I-1987 respectively), 25 rue du docteur Roux, 75724 Paris, France, on Mar. 3$^{rd}$, 1998. The strain *S. thermophilus* BF11116 (CNBL 1177) was deposited under the Budapest Treaty at the Belgian Coordinated Collections of Microorganisms LMG P-18997, K. L. Ledeganckstraat 35, B-9000 Gent, Belgium, on Jul. 5, 1999. All restrictions as to the availability of these deposits will be withdrawn upon first publication of this application or another application which claims benefit of priority to this application.

The invention is also directed to compositions for the health of the mouth that comprise a lactic bacteria that is not part of the resident microflora of the mouth, that is low acidifying, and that is capable of adhering directly to the pellicle of the teeth. The compositions are particularly intended for the prophylaxis or the treatment of dental caries, dental plaque, and periodontal infection. The lactic bacteria strain may be selected from the group consisting of *Streptococcus thermophilus, Lactococcus lactis* subsp. *lactis*, and *Lactococcus lactis* subsp. *lactis biovar diacetylactis* and preferably from the group consisting of the strains CNCM I-1984, CNCM I-1985, LMG P-18997, CNCM I-1986, and CNCM I-1987. In these compositions the lactic bacteria strains may be genetically modified as described above.

The lactic bacteria strains may be included in a food, pet food, cosmetic, or pharmaceutical composition, for example. Accordingly, the compositions are preferably a toothpaste, mouth rinse, gum, spray, beverage, candy, infant formula, ice cream, frozen dessert, sweet salad dressing, milk preparation, cheese, quark, yogurt, acidified milk, coffee cream, or whipped cream, for example.

In the compositions of the invention, the lactic bacteria strains may be included alone or in combination with milk derivatives, for example, in order to obtain synergistic preparations. Accordingly, these compositions for the health of the mouth comprise:

a lactic bacteria that is not part of the resident microflora of the mouth, which is capable of adhering directly to the pellicle of the teeth;

any forms of lactic glycopeptides, renneted milk, or bacteriocin.

Figure 2:
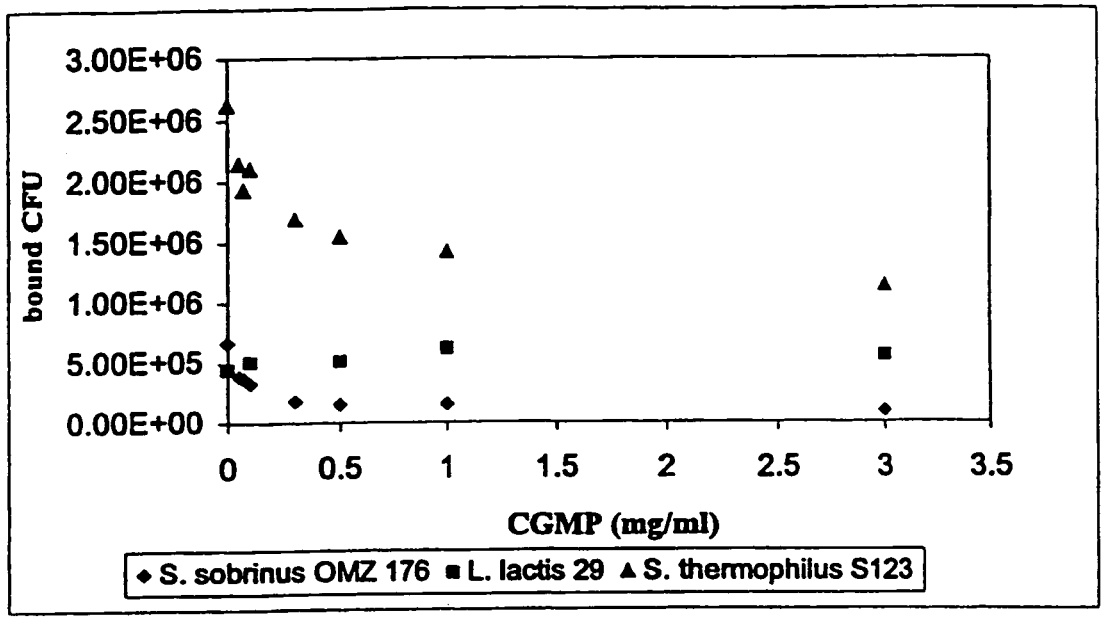
FIG. 2 represents the effect of CGMP on the adhesion to S-HA beads of *S. sobrinus* OMZ 176, *L. lactis* NCC2211, and *S. thermophilus* NCC1561.
Figure 3:
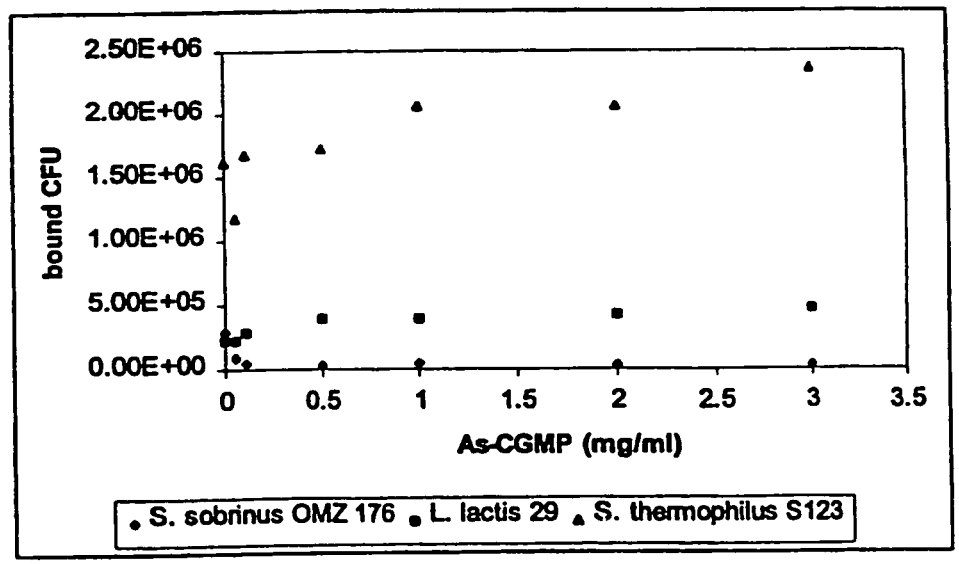
FIG. 3 represents the effect of As-CGMP on the adhesion to S-HA beads of *S. sobrinus* OMZ 176, *L. lactis* NCC2211, and *S. thermophilus* NCC1561.

The lactic glycopeptides are preferably caseino-glycomacropeptides (CGMP), fluorinated or non-fluorinated micellar casein (which can be obtained as described in EP 0 604 802 and EP 0 748 591), or renneted milk. The caseino-glycomacropeptides are preferably added in a minimum amount of about 0.1%. It has also been shown that the caseino-glycomacropeptides do not prevent the lactic bacteria from adhering to the teeth pellicle (FIGS. 2 and 3).

Synergistic compositions may also be prepared by adding at least one bacteriocin which is active against Gram-positive oral bacteria. In this embodiment the oral hygiene compositions may comprise 0.00001 to 50%, and preferably from 0.00001 to 15% of purified bacteriocin, by weight of the composition. The bacteriocin is preferably variacin (EP 0759469).

To protect the composition from degradation, an oil-soluble antioxidant may also be included. Suitable antioxidants include the "tocopherols," butyl-hydroxyanisole (BHA), butyl-hydroxytoluene (BHT), and ascorbyl palmitate. The oil soluble antioxidant is present in amounts of from 0.005% to 0.5%, preferably 0.005% to 0.01% by weight of the composition.

Suitable abrasives for use in dentifrice compositions of the present invention include calcium carbonate, calcium aluminosilicate, alumina hydrates, alumina, zinc orthophosphate, plastic particles, and silica, of which silica is the preferred abrasive.

Compositions according to the invention will have a pH which is orally acceptable and within a range such that the activity of the lactic bacteria is not compromised. The pH may be in the range of 3.0 to 9.5, preferably in the range 3.5 to 6.5.

The compositions of the invention may be prepared by conventional processes that comprise admixing the ingredients together in the appropriate relative amounts and finally, if necessary, adjusting the pH to the desired value.

The present invention also relates to a composition for maintaining the health of the mouth by reducing the colonization of *A. naeslundii* in mammals, said composition comprises an exogenous lactic bacteria, which has been selected for its ability to adhere to the tooth surface and to produce a growth inhibition factor.

These compositions are particularly intended for the prophylaxis or the treatment of dental plaque and infection related to *A. naeslundii* disease such as root caries, for example.

The lactic bacteria strain according to the present invention is selected from the group consisting of *Streptococcus thermophilus, Lactococcus lactis* subsp. *lactis*, and *Lactococcus lactis* subsp. *lactis biovar diacetylactis* and preferably from the group consisting of the strains CNCM I-1984, CNCM I-1985, CNCM I-1986 and CNCM I-1987.

Such a composition may contain at least $10^4$-$10^9$ cfu/g of lactic bacteria.

*Actinomyces naeslundii* genospecies 1 (formerly *A. naeslundii*) and 2 (formerly *A. viscosus*) are among the strongest plaque forming oral strains. They are commonly isolated at root caries sites, in particular in humans over 40 years, and they are believed to be the major etiological agent of this disease.

Thus, the invention also provides a method for the prevention or the treatment of *Actinomyces naeslundii*-related infections in mammals, particularly dental plaque extent and root caries, comprising the step of feeding the mammal a composition containing at least one lactic bacteria strain selected for its ability to adhere to the tooth surface and to produce a growth inhibition factor.

The amount to be administered may be of at least about $10^4$-$10^9$ cfu/g of lactic bacteria.

The invention is further directed to a method for screening lactic bacteria capable of adhering to tooth. This method comprises the steps of:

(1) preparing monoclonal antibodies that recognize specific surface proteins of a lactic bacteria strain capable of adhering to the teeth, and (2) screening any lactic bacteria strain by using the monoclonal antibody of strain capable of adhering to the teeth.

The monoclonal antibodies are used as a tool to detect the said lactic bacteria strain among other strains growing nearby.

EXAMPLES

The present invention is not to be limited in scope by the specific embodiments described herein. Indeed, various modifications of the invention, in addition to those described herein, will become apparent to those skilled in the art from the foregoing description. Such modifications are intended to fall within the scope of the claims. Various publications are cited herein, the disclosures of which are incorporated by reference in their entireties to the extent necessary for understanding the present invention. DNA manipulation, cloning and transformation of bacteria cells are, except where otherwise stated, carried out according to the textbook of Sambrook et al. (Sambrook et al., Molecular Cloning, A Laboratory Manual, Cold Spring Harbor Laboratory Press, U.S.A., 1989).

The examples are preceded by a brief description of the plasmids, strains, and the various media used, as well as the method for producing a monoclonal antibody.

Example 1

Strains and Culture Conditions

More than 100 strains (belonging to the Nestle culture collection) were screened for their ability to attach to saliva-coated hydroxyapatite beads, and in particular the following 23 strains: S. thermophilus Y54 (NCC 2284), S. thermophilus 5fi6 (NCC 1971), S. thermophilus Sfi13 (NCC 2008), S. thermophilus Sfi21 (NCC 2038), S. thermophilus Sfi39 (NCC 2130), S. thermophilus Sfi42 (NCC 2145), S. thermophilus Sfi47 (NCC 2172), S. thermophilus S118 (NCC 1529), S. thermophilus S119 (NCC 1536), S. thermophilus S122 (NCC 1554), S. thermophilus S123 (NCC 1561), S. thermophilus S126 (NCC 1587), L. lactis subsp. cremoris 15 (NCC 92), L. lactis subsp. cremoris 25 (NCC 1932), L. lactis subsp. cremoris 136 (NCC 2419), L. lactis subsp. diacetylactis 8 (NCC 1970), L. lactis subsp. diacetylactis 28 (NCC 2057), L. lactis subsp. diacetylactis 69 (NCC 2225), L. lactis subsp. diacetylactis 80 (NCC 2272), L. lactis subsp. lactis 29 (NCC 2211), L. lactis subsp. lactis 50 (NCC 2224), L. lactis subsp. lactis 54 (NCC 2228), S. macedonicus 216 (NCC 2484).

The 5 oral strains, S. sobrinus OMZ 176, S. oralis OMZ 607, A. naeslundii OMZ 745, V. dispar OMZ 493 and F. nucleatum OMZ 596 were obtained from the Institute fur Orale Mikrobiologie und Aligemeine Immunologie, University of Zürich and were cultured in FUM medium in anaerobiosis (GasPackSystem, BBL) at 37° C.

All the strains were stored in glycerol at −20° C. and pre-cultured for 14 hours prior to use at their specific optimal temperature; S. sobrinus OMZ 176 grew in FUM medium lactococci and streptococci in M 17 (Difco) except S. thermophilus NCC1529, Si 19, S122, NCC1561 and S126 that grew in Belliker (prepared by dissolution of 20 g tryptone, 5 g yeast extract, 2.5 g gelatine, 5 g dextrose, 5 g sucrose, 5 g lactose, 4 g NaCl, 0.5 g Ascorbic acid, and 10 g beef extract in 1 L of water).

For plate counting, S. sobrinus OMZ 176 was cultured in Mitis-Salivarius agar (Difco), S. thermophilus NCC1529, S119, S122, NCC1561, BF11116, and S126 in Belliker agar (prepared by adding to liquid Belliker 15 g of Bacto agar, Difco), and the remaining lactic bacteria strains in M17 agar (Oxoid).

Example 2

Production of Monoclonal Antibody

A monoclonal antibody would be used as a tool to detect L. lactis subsp. lactis NCC22111 among 5 oral strains growing together on S-HA discs and forming a biofilm that simulates dental plaque. Therefore the monoclonal antibody was tested against these strains to verify there was no cross-reaction. To this end, the monoclonal antibody is produced as described by Granato et al. "A mouse monoclonal IgE antibody anti-bovine milk lactoglobulin allows studies of allergy in the gastrointestinal tract., Clin. Exp. Immunol., 63, 703-710, 1986.

Example 3

Selection of Adherent Lactic Bacteria

Attachment to Saliva-coated Hydroxyapatite Beads (S-HA)

To select among the lactic bacteria dairy strains those strains that are able to attach to saliva-coated hydroxyapatite beads (S-HA), the procedure previously described by Neeser et al. (1994) was used with slight modification in that the bead washings were done with 150 µl volumes and Hyamine hydroxide was substituted with Benzethonium hydroxide (Sigma).

Briefly, all the strains were grown to the end of the log phase in FUM except S. thermophilus NCC1529, S119, S122, NCC1561, and S126 that were cultured in Belliker. S. sobrinus OMZ 176, L. lactis subsp. lactis NCC2211, 50 and 54, S. thermophilus NCC1529, S119, S122, NCC1561, and S126 grew at 37 C°, the remaining lactococci at 30° C., and the remaining streptococci at 42° C.

5 mg of hydroxyapatite beads (BDH Chemicals Ltd, Poole, England) were covered with 70 µl clarified saliva obtained from volunteers in the lab and prepared as previously explained (Neeser et al, 1-994). Saliva coated beads were kept overnight at 4° C., then washed (first with distilled water and after with HEPES buffer) and finally inoculated with 100 µl of metabolically labeled bacterial suspension (bacteria had been grown in medium supplemented with 10 µCi/ml $^{14}$C acetic acid). Adhesion took place during 45 min at 37° C., then unbound bacteria were washed away and the attached cells directly counted in a LKB scintillation counter (type 1219 Rackbeta).

Adhesion percentages are expressed as radioactivity bound to the beads relative to the total radioactivity added to each well. All measurements were done in triplicate. Table 2 reports the percentages of adhesion to saliva-coated hydroxyapatite beads obtained for several screened strains and for S. sobrinus OMZ 176 (the reference strain).

TABLE 2

Percentages of Adhesion to Saliva-coated Hydroxyapatite Beads for Several Screened Strains

| STRAIN | % ADHESION (±SD) |
| --- | --- |
| S. sobrinus OMZ 176 | 2.23 ± 0.49 |
| S. thermophilus Sfi42 (NCC 2145) | 0.08 ± 0.02 |
| S. thermophilus Sfi47 (NCC 2172) | 0.14 ± 0.04 |

TABLE 2-continued

Percentages of Adhesion to Saliva-coated Hydroxyapatite Beads for Several Screened Strains

| STRAIN | % ADHESION (±SD) |
|---|---|
| S. thermophilus NCC1529 | 2.89 ± 0.60 |
| S. thermophilus S119 (NCC 1536) | 0.15 ± 0.04 |
| S. thermophilus S122 (NCC 1554) | 0.93 ± 0.17 |
| S. thermophilus NCC1561 | 2.19 ± 0.50 |
| S. thermophilus S126 (NCC 1587) | 1.19 ± 0.56 |
| L. lactis subsp. diacetylactis 28 (NCC 2057) | 1.59 ± 0.17 |
| L lactis subsp. diacetylactis NCC2225 | 1.96 ± 0.40 |
| L. lactis subsp. diacetylactis 80 (NCC 2272) | 1.20 ± 0.35 |
| L lactis subsp. lactis NCC2211 | 2.85 ± 0.85 |

Four strains, S. thermophilus NCC 1529 (CNCM 1-1984), S. thermophilus NCC1561 (CNCM 1-1985), L. lactis subsp. lactis NCC2211 (CNCM 1-1986) (hereinafter L. lactis NCC2211) and L. lactis subsp. diacetylactis NCC2225 (CNCM 1-1987) showed adhesion values close to S. sobrinus OMZ 176.

L. lactis NCC2211 and S. thermophilus NCC1561 were chosen as the more promising candidates since they grow very well at 37° C., which is the temperature in the mouth, while L. diacetylactis NCC2225 has an optimal growth temperature of 30° C. In particular, L. lactis NCC2211 cannot grow on sucrose, but it can ferment a wide range of sugars, moreover other oral strain can provide glucose via their invertase.

Adhesion Saturation Curves

Figure 1B:
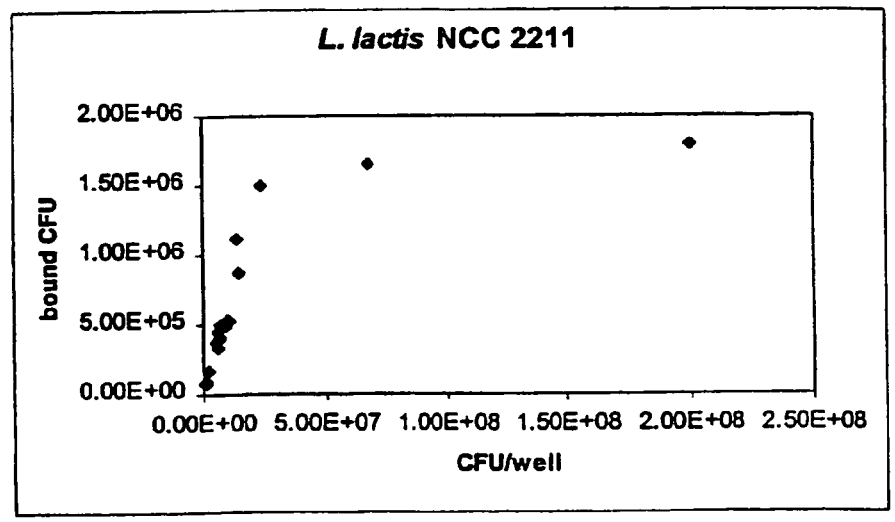
Figure 1C:
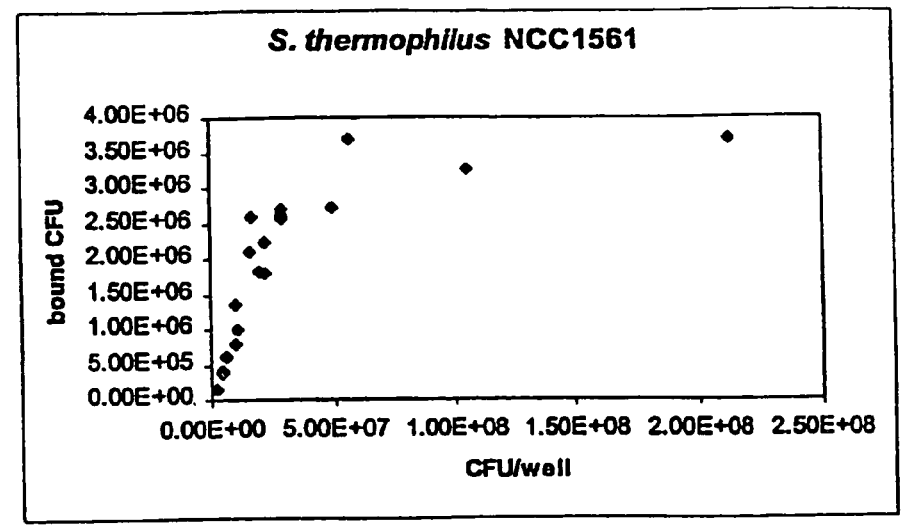

Curves of bound CFU versus CFU inoculated into the well were determined to verify if bead saturation could be obtained. The 50% saturation was obtained directly from the bending point of the curves. The adhesion saturation curves for S. sobrinus OMZ 176, L. lactis NCC2211, and S. thermophilus NCC 1561 were determined. They are shown in FIG. 1.

For each of the three strains the CFU number inoculated in the well to get 50% bead saturation and the corresponding number of bound CFU were directly deduced from the bending point of the curves and are given in the table 3.

TABLE 3

Number of CPU Inoculated Per Well to get 50% Bead Saturation

| | cfu/well | Bound cfu | % adhesion |
|---|---|---|---|
| S. sobrinus OMZ 176 | 4.00E +07 | 4.00E+06 | 10% |
| L. lactis NCC2211 | 1.00E+07 | 9.00E−f-05 | 9% |
| S. thermophilus NCC1561 | 3.00E+07 | 2.00E+06 | 7% |

Example 4

Effect of Caseino-glycomacropeptides

The influence of CGMP on the adhesion of L. lactis NCC2211 and S. thermophilus NCC 1561 was studied to verify the possibility of using CGMP to foster the predominance of one of these two strains over pathogenic strains, namely S. Sobrinus OMZ 176. Caseino-glycopeptide (CGMP) and its desialylated derivative (As-CGMP) were obtained from Nestec S. A., Lausanne (for their preparation see Neeser et al., 1994).

The dose-response effect was studied on the adhesion to S-HA beads by inoculating, in the well, 100 μl of bacterial suspension (CFU/ml corresponding to the 50% bead saturation previously calculated) which contained CGMP or AsCGMP in different concentrations and then performing the adhesion assay in the usual manner. Concentrations in the range 0.05 to 3 mg/ml were tested. No previous incubation of the bacteria in presence of CGMP or As-CGMP was done.

FIG. 2 provides the curves obtained for the three strains by plotting the number of bound cells versus increasing amounts of CGMP, the number of inoculated cells corresponds to 50% bead saturation formerly calculated for each strain. The strong inhibition observed in the case of S. sobrinus OMZ 176 confirms the previous results obtained by Neeser et al. (1994) and Schupbach et al. (J. Dent. Res., 75, 1779-1788, 1996).

FIG. 2 shows that 0.25 mg/ml produced 50% inhibition of the adhesion of S. sobrinus OMZ 176, while more than 2 mg/ml were necessary to have the same effect with S. thermophilus NCC1561. CGMP slightly enhances the adhesion of L. lactis NCC2211.

As in the case of CGMP, the desyalilated derivative inhibits the adhesion of S. sobrinus OMZ 176; only 0.05 mg/ml are needed to produce 50% decrease in the adhesion percentage. As-CGMP does not influence L. lactis NCC2211 adhesion, while it slightly fosters the adhesion of S. thermophilus NCC1561 (FIG. 3).

Example 5

Toothpaste

Toothpaste is prepared by adding $10^5$ cfu/ml of at least one of the lactic bacteria strain CNCM I-1984, CNCM I-1985, CNCM I-1986, CNCM I-1987 or LMG P-18997 in a lyophilized form, to a mixture containing: 1.65% Cetyl pyridinium chloride, 33.0% Sorbitol (70% soln), 25.0% Glycerin, 2.0% Sodium carboxymethyl cellulose, 0.25% Sodium fluoride, 26.3% Silica (RP 93), 8.1% Thickening Silica (Sident 22), 0.5% Sodium saccharine, 3.2% Poloxamer (Pluronic F108).

The toothpaste is intended for the prophylaxis or the treatment of dental caries, dental plaque and periodontal infection.

Example 6

Ice Cream

A cream comprising 10.8% lactic fats, 13.5% milk solids (non fat), 0.3% Emulstab® SE30 and 0.3% Emulstab® foam (Grindsted, DK) is prepared and then pasteurized at 105° C. for 20s, homogenized at 75° C. and 300 bar, cooled to 38° C., and inoculated with pre-cultures in MRS medium, taken in the exponential growth phase, at a rate of $10^7$ to $10^8$ cfu/ml of at least one of the lactic bacteria strain of CNCM 1-1984, CNCM 1-1985, CNCM 1-1986, CNCM 1-1987 or LMG P-18997. The cream is then fermented for 10 hours at 38° C. up to a pH of about 4.5. At the end of the fermentation, sucrose and glucose syrup is added thereto. The composition of the cream is presented in table 4 below. The mixture is then beaten, cooled to 4° C., stored at 4° C., and chilled to a degree of expansion of 95° C. by volume.

TABLE 4

Ice Cream Composition

| Ingredients | Composition (kg) | Fats (%) | Non-fat solids (%) | Sucrose (%) | Solids content (%) |
|---|---|---|---|---|---|
| Cream (35%) | 30.83 | 10.79 | 1054 | | 12.33 |
| Powdered skim milk | 12.45 | | 11.95 | | 11.95 |
| Emulstab ® SE30 | 0.41 | | | | 0.37 |
| Emulstab ® foam | 0.41 | | | | 0.36 |
| Water | 55.91 | | | | |
| Total: cream base | 100.00 | 10.79 | 13.49 | — | 25.01 |
| Cream base | 74.14 | 8.00 | 10.00 | — | 18.54 |
| Sucrose | 22.06 | | | 15.00 | 15.00 |
| Glucose syrup | 3.80 | | | | 3.00 |
| Fermented ice cream | 100.00 | 8.00 | 10.00 | 15.00 | 36.54 |

Example 7

Yogurt

5 L MRS culture medium were sterilized for 15 min at 121° C. and then inoculated with 5% by volume of an active culture of at least one of the S. Thermophilus strain CNCM I-1984, CNCM I-1985, or LMG P-18997 containing approximately $10^9$ cfu/ml. After incubation for 8 h at 41° C., a starter containing 4.5×$10^8$ cfu/ml was obtained.

5 L reconstituted skimmed milk having a dry matter content of 10%, to which 0.1% yeast extract had been added, was sterilized for 15 min at 121° C. and inoculated with 2% of an active culture of commercial thickening Streptococcus thermophilus containing approximately $10^9$ cells/ml. After incubation for 4 h at 41° C., a starter containing 4.5×$10^8$ cells/ml was obtained.

One batch of whole milk containing 3.7% fats strengthened with 2.5% skimmed milk powder and then pasteurized for 30 min at 90° C. was then inoculated with 2% by volume of the starter of at least one of the strains CNCM I-1984, CNCM I-1985 or LMG P-18997 strains and 3% by volume of the starter of thickening Streptococcus thermophilus. The inoculated milk is stirred, poured into pots, and incubated for 4 h at 41° C. The resulting yogurt obtained has a good firm and smooth texture and is intended for the health of the mouth.

Example 8

Chewing Gum

A chewing gum for preventing or treating dental caries, dental plaque, or periodontal infection can be prepared adding an active culture of at least one of the S. Thermophilus strains CNCM I-1984, CNCM I-1985, or LMG P-18997, so that it contains approximately $10^4$ to $10^9$ cfu/g, to the following typical ingredients: 67.5% Xylitol, 20% Gum base, 5% Calcium carbonate, 3% Glycerin, 2% Pluronic F127, 1% Cellulose gum, 0.5% Balast compounds and 1% Flavor.

Example 9

Pet Food Composition

A pet food for mouth health is obtained by preparing a feed mixture made up of corn, corn gluten, chicken and fish meal, salts, vitamins, and minerals. The feed mixture is fed into a pre-conditioner and moistened. The moistened feed leaving the pre-conditioner is then fed into an extruder-cooker and gelatinised. The gelatinised matrix leaving the extruder is forced through a die and extruded. The extrudate is cut into pieces suitable for feeding to dogs, dried at about 110° C. for about 20 minutes and cooled to form pellets which have a water activity of about 0.6. The pellets are sprayed with 3 coating mixtures. Each coating mixture contains active culture of at least one of the S. Thermophilus strains CNCM I-1984, CNCM I-1985, or LMG P-18997 but one coating mixture uses hydrogenated soy fat as a coating substrate, one coating mixture uses water as a coating substrate, and one coating mixture uses protein digest as a coating substrate. The pellets contain approximately $10^4$ to $10^9$ cfu/g of the said strains.

Example 10

In-vitro Trials

The strains S. thermophilus NCC 1561 (CNCM I-1985) and L. lactis subsp. lactis NCC2211 (CNCM I-1986) (hereinafter L. lactis NCC2211) were incorporated in vitro in a biofilm mimicking dental plaque in vitro.

The oral strain A. naeslundii genospecies 1 (formerly A. naeslundii) OMZ745 and A. naeslundii genospecies 2 (formerly A. viscosus) OMZ105 were obtained from the Institute für Orale Mikrobiologie und Allgemeine Immunologie, University of Zürich and they were cultured in FUM medium in anaerobiosis (GasPackSystem, BBL) at 37° C.

All the strains were stored in glycerol at −20° C. and precultured for 14 hours prior to use at their specific optimal temperature;

The two selected strains L. lactis NCC2211 and S. thermophilus NCC1561 were inoculated in an in vitro. system in which a biofilm, composed by bacteria commonly found in the human mouth after 40 years, developed on saliva coated-hydroxyapatite discs. Fluid Universal Medium (FUM), the growth medium used, was especially formulated to buffer the acidity produced by the test strains and to have therefore a continued growth (plaque development), like it is in the mouth (Gmur and Guggenheim, 1983). The assays were done in triplicate and the mixtures with and without the dairy strains were tested in parallel. The strains listed in the Table 5 were used.

TABLE 5

Bacterial strains used and culture conditions applied in the in vitro dental plaque experiments.

| Strain | Relevant properties | Growth conditions |
|---|---|---|
| S. thermophilus NCC1561 | S-HA adherent | FUM, Belliker; 37° C. |
| L. lactis subsp. lactis NCC2211 | S-HA adherent | FUM, M17-lactose; 37° C. |
| S. sobrinus OMZ176 | Cariogenic | FUM; 37° C. |
| S. oralis OMZ607 | Plaque forming | FUM; 37° C. |
| A. naeslundii OMZ745 | Plaque forming root caries causative agent | FUM; 37° C. |
| V. dispar OMZ493 | Plaque forming | FUM; 37° C. |
| F. nucleatum OMZ596 | Plaque forming | FUM; 37° C. |

Procedure

Saliva pellicle formation: cover synthetic hydroxyapatite discs of 10 mm diameter (HY-APATITE®, Euro-Crystals, Landgraaf, The Netherlands) with 800 µl of human saliva and incubate for 4 h at room temperature under shaking (1 disc/well in a 24 holes sterile Nunclon plate).

Bacterial consortium preparation: grow S. thermophilus NCC1561, L. lactis subsp. lactis NCC2211, S. sobrinus OMZ176, S. oralis OMZ607, A. naeslundii OMZ745, V. dispar OMZ493 and F. nucleatum OMZ596 overnight at 37° C. in anaerobiosis in FUM-glucose (S. thermophilus NCC1561 in FUM-lactose), adjust the $OD_{550}$ to 1 with FUM and pool 2 ml of each oral bacterial suspension with 2 ml of either S. thermophilus NCC1561 or L. lactis subsp. lactis NCC2211. The control mixture contains the five oral strains only.

Biofilm formation and recovery: the procedure is as described in Guggenheim et al., 1998, Validation of a new biofilm model. J. Dent. Res. 77, (Spec Iss A): 110 (Abstract #38).

Cultural analysis of the biofilm: spiral plate the suspension on Columbia Blood Agar (5% sheep blood, Becton Dickinson, Meylan Cedex, France) for the total count and for the differentiation of A. naeslundii. Incubate the plates at 37° C. in anaerobiosis for 48 h.

GROWTH Antagonism Between the Oral and the Dairy Strains Under Study

Strains and culture conditions used are listed in the Table 6.

TABLE 6

Bacterial strains used and culture conditions applied in the growth antagonism experiments.

| Strain | Relevant properties | Growth conditions |
|---|---|---|
| S. thermophilus NCC1561 | S-HA adherent | Belliker; 42° C. |
| L. lactis subsp. lactis NCC2211 | S-HA adherent | M17-lactose; 37° C. |
| S. thermophilus NCC1536 | non-adherent | Belliker; 42° C. |
| A. naeslundii OMZ745 | plaque forming | BHI, 37° C.; anaerobiosis |
| A. viscosus OMZ105 | plaque forming | BHI; 37° C. |

S. thermophilus NCC1561, S. thermophilus NCC 1536 and L. lactis NCC2211 (killer strains) were tested for growth antagonism against A. naeslundii OMZ745 and A. viscosus OMZ105 (target strains).

Procedure

Grow the killer strains overnight on agar plates in anaerobiosis and the target strains in BHI until middle stationary phase Dilute 20 µl of the target strains suspension in 3 ml of BHI soft agar (agar 7 g/l) containing glucose and lactose, vortex and pour immediately on a BHI agar plate Solidify for 1 h at room temperature, then streak the killer strain from the M17 plate in the form of a cross. Streak in parallel the killer and the target strains alone as a control Incubate at 37° C. in anaerobiosis for 24 hours Growth antagonism is revealed by an inhibition halo around the cross.

Statistics

Differences between the control and test consortia were determined by Student's t test.

Results and Discussion

S. thermophilus NCC1561 and L. lactis NCC2211 could be incorporated and grown in the plaque-like biofilm on the S-HA discs, and their total CFU/disc after 40.5 h are given in the Table 7.

TABLE 7

Level of incorporation of the two dairy strains in the biofilm (CFU/disc). The values are the mean of three experiments with their standard deviations.

| Method of inoculation | S. thermophilus NCC1561 ($\times 10^6$) | L. lactis NCC2211 ($\times 10^6$) |
|---|---|---|
| Together with the oral strains | 4.08 +/− 1.78 | 5.76 +/− 3.64 |
| Before the oral strains | 5.03 +/− 2.21 | 3.87 +/− 4.01 |

The effect of incorporating the dairy strains in the biofilm on the oral species is indicated in the Tables 8 and 9. When S. thermophilus NCC1561 was included (Table 8), a general decrease of the total flora, that is represented by the counts on Columbia blood agar plates (CBA), and of 4 of the oral species was noticed.

When L. lactis NCC2211 was introduced in the oral strains consortium (Table 9) the total flora counts notably diminished (CFU on CBA). The decrease was significant in the case of A. naeslundii OMZ745 that significantly diminished (p=0.021) The decrease was even stronger if the strain was inoculated on the discs before the oral bacteria.

TABLE 8

Modulation of the oral strains consortium by S. thermophilus NCC1561 (CFU/disc).

| Treatment | CBA ($\times 10^8$) | A. naeslundii OMZ745 ($\times 10^6$) | MS ($\times 10^8$) |
|---|---|---|---|
| Control | 2.86 +/− 2.14 | 5.29 +/− 2.58 | 2.02 +/− 1.68 |
| +NCC1561 | 1.63 +/− 0.55 | 4.75 +/− 1.45 | 1.21 +/− 0.81 |
| Pre-incubation with NCC1561 | 2.32 +/− 0.38°° | 4.78 +/− 2.29 | 1.48 +/− 0.29 |

N = 3.
*p-values are calculated in respect to the control (*p < 0.05; **p < 0.01);
°p-values are calculated in respect to the "+NCC1561" treatment (°p < 0.05; °°p < 0.01).

TABLE 9

Modulation of the oral strains consortium by L. lactis NCC2211 (CFU/disc).

| Treatment | CBA ($\times 10^8$) | A. naeslundii OMZ745 ($\times 10^6$) | MS ($\times 10^8$) |
|---|---|---|---|
| Control | 2.77 +/− 2.16 | 6.07 +/− 2.70 | 3.04 +/− 2.88 |
| +NCC2211 | 0.65 +/− 0.33 | 4.59 +/− 2.81 | 0.65 +/− 0.33* |
| Pre-incubation with NCC2211 | 0.27 +/− 0.11**° | 3.91 +/− 3.29*° | 0.27 +/− 0.11**°° |

N = 3.
*p-values are calculated in respect to the control (*p < 0.05; **p < 0.01);
°p-values are calculated in respect to the "+NCC2211" treatment (°p < 0.05; °°p < 0.01).

Some assays were carried out to verify if the reduction of the oral strains was due to growth antagonism of the dairy strains towards them (Table 10). The strains A. viscosus OMZ105 and S. thermophilus NCC1536 were also included in the test since they are part of the in vivo model (Example 11)

All the four dairy strains inhibited the growth of the Gram-negative strain A. viscosus OMZ105. This inhibition cannot be attributed to lactic acid production. A. viscosus is able to metabolize lactate only under aerobic conditions (van der Hoeven et al. (1990) *Oral Microbiol. Immunol.* 5, 223-225) and it is very aciduric. These findings have been confirmed by plating *A. viscosus* in presence of 1% lactic acid: no inhibition was observed.

TABLE 10

Oral strains growth inhibition by *S. thermophilus* NCC1561, *S. thermophilus* NCC1536 and *L. lactis* NCC211.

| Target | KILLER STRAINS | | | Lactic acid 1% |
|---|---|---|---|---|
| | NCC1561 | NCC1536 | NCC2211 | |
| *A. naeslundii* OMZ745 | + | + | + | − |
| *A. viscosus* OMZ105 | + | + | + | − |

CONCLUSIONS

*S. thermophilus* NCC1561 and *L. lactis* NCC2211 could be incorporated in a biofilm mimicking dental plaque and were able to modulate the oral microflora, significantly reducing the number total of cfu, and more specifically, these strains were able to significantly decrease the colonization extent of *A. naeslundii* genospecies 2. In addition the strains could inhibit the growth of *A. naeslundii* genospecies 1 and 2 in co-cultures.

Example 11

In-vivo Trials

An in-vivo study was performed on a rat model. In this study, the association of the selected strains was continued during the whole experimental period on a daily basis, by the way of a chilled dairy product feeding.

The study was carried out in 58 days. In order to perform the experiment during the day, the active period of the animals had to be advanced of 7 hours totally; this was done in three steps on day 16, 17 and 18 as further described in detail. The cariogenic strains were associated on days 21 and 22, while association of the dairy strains started on day 23 and lasted until day 57. The animals were fed the dairy strains as supplement in a yogurt base that was included in the normal diet, as explained in the section. The rats teeth were swabbed at the end of the study, on day 58.

Animals and Diet 10 litters consisting of 4 Osborne-Mendel rats pups each (animal production section of the Institute für Orale Mikrobiologie und Allgemeine Mikrobiologie, University of Zurich, Zurich, Switzerland) were used in the experiment. All animals were weighed at the beginning and at the end of the experimental period. When 13 days old, the dams and the pups were transferred to screen-bottom stainless-steel cages without bedding and nourished with low-fluoride powdered (0.2 μm) Nafag diet to avoid fissure impaction (Rat Checkers No. 184, NAFAG, Gossau SG, Switzerland), and tap water *ad libitum*. The active phase during which the rats eat is during the night, i.e. 18:00-06:00.

In order to allow refilling of the food cups during normal working hours, the circadian biorhythm was stepwise reversed between days 16 and 18 by advancing the active phase of the rats each day on three occasions by adjusting the automatic light controls.

On day 16/17 the beginning of the active period was brought forward from 18:00 h to 15:00 i.e. it was night from 15:00-03:00 and it was day onwards. On day 17/18 the beginning of the active period was brought forward from 15:00 to 12:00 h, i. e. it was night from 12:00 h-00:00 h and day from 00:00 h onwards.

Finally on day 18/19 the beginning of the active period was brought forward from 12:00 to 10:00 i.e. it was night from 10:00 h to 22:00 h and day from 22:00 h onwards.

Therefore by day 19 the shift of the active phase for the rats from the hours of darkness to normal working hours (10:00-22:00 h) was completed.

On day 20 the dams were removed, and the rats started to be fed *ad libitum* with the modified diet 2000a containing 40% sucrose, 28% substitute for skim milk (soya protein extract SVPRO-PP 1611 39.4%, lactose 49.3%, 0.6%, L-Methionine 0.3%, L-Lysine HCl 0.1%), 24% wheat flour, 5% brewer's yeast, 2% Gevral® Instant Protein (Whitehall-Robins SA, 6301 Zug, Switzerland) and 1% NaCl.

During the association period (days 21 and 22) the drinking water was supplemented with 2% glucose and 2% sucrose to support the implantation of the associated bacteria. On day 23 the litters were distributed among the 3 treatments, 1 animal per cage, in a programmed feeder machine and began to receive the test diet as indicated in the table 13. The test diet consisted of 18 yogurt meals containing the test strains alternating with 18 meals of the modified diet 2000a previously described.

Drinking water was supplied *ad libitum*. Following the swabbing procedure on day 58 the animals were overdosed with Thiopental sodium (100 mg/Kg of body weight) given by intra-peritoneal injection and decapitated when comatose.

Bacterial strains: The strains listed in the Table 11 were used.

TABLE 11

Bacterial strains that were used in this study

| Strain | Relevant properties | Growth conditions |
|---|---|---|
| *S. thermophilus* NCC1561 | S-HA adherent | Belliker; 42° C. |
| *S. thermophilus* NCC1536 | Non-adherent control | Belliker; 42° C. |
| *L. lactis* NCC2211 | S-HA adherent | M17-lactose; 37° C. |
| *A. viscosus* OMZ105 | Plaque forming, S-HA adherent | BHI; 37° C. |

Preparation of the Tested Lab Strains for the Association.

A preliminary study was done to assess the growth parameters, especially the hours required to reach the stationary phase in the specific conditions further described. It was therefore established to grow the *S. thermophilus* strains for 7 h and the *L. lactis* one for 6 h. Also a study of the viability after freezing of the dairy strains was performed by plating the same cell suspension before and after freezing. In order to be associated to the animals, the dairy strains were treated according to the following procedure.

Procedure

Inoculate the strains 1% overnight in their proper medium from a glycerol stock

Inoculate them 5% from this culture into 10 batches of 4 liters of their proper medium pre-heated at the optimal growth temperature, and grow them until the end of the log phase/beginning stationary phase Determine the final CFU/ml by plating on M17-lactose agar from two randomly chosen batches for each of the 4 strains. Incubate the plates overnight in anaerobiosis.

Centrifuge the cultures from each batch at 6000 rpm for 10 min and re-suspend the pellets in 150 ml of fresh medium; keep overnight at 4° C.

Centrifuge again and re-suspend in the freezing medium (15% glycerol in Belliker or M17).

Split in aliquots in order to have $2\times10^{11}$ viable cells/vial, taking into account the viability loss due to freezing, and store at −20° C. until needed.

Association of the Animals with the Bacterial Strains

The animals were arranged in 3 treatments (Table 12). Each treatment consisted of 10 pups that were distributed in 1 per cage.

TABLE 12

Arrangement of the treatments.

| Treatment | Associated bacteria |
|---|---|
| 1 | *A. viscosus* OMZ105; *S. thermophilus* NCC1536 |
| 2 | *A. viscosus* OMZ105; *S. thermophilus* NCC1561 |
| 3 | *A. viscosus* OMZ105; *L. lactis* NCC2211 |

All rats were first infected on days 21 and 22 with *A. viscosus* OMZ105.

The tested LAB strains were associated daily (since contained in the yogurt base meal), starting on day 23. 2 frozen vials, each containing $2\times10^{11}$ viable cells of the test strain, were mixed in 200 ml of yogurt in order to have at least $10^9$ CFU/ml. *S. thermophilus* NCC 1536, a non S-HA adhering strain, was used as a negative control.

The yogurt and diet 2000a meals, of 1 ml and 400 mg respectively, were offered alternatively 18 times per day at 20-min intervals (Table 13). Therefore, each animal received in total 18 ml of yogurt and 7.2 g of powdered diet.

The meals were dispensed in the food cups of a programmed feeder machine that automatically offered to the animals the right meal at the exact time.

TABLE 13

Eating times.

| N° of the meal | High cariogenic meals | Yogurt meals | N° of the meal |
|---|---|---|---|
| 1 | 10:00 | 10:20 | 2 |
| 3 | 10:40 | 11:00 | 4 |
| 5 | 11:20 | 11:40 | 6 |
| 7 | 12:00 | 12:20 | 8 |
| 9 | 12:40 | 13:00 | 10 |
| 11 | 13:20 | 13:40 | 12 |
| 13 | 14:00 | 14:20 | 14 |
| 15 | 14:40 | 15:00 | 16 |
| 17 | 15:20 | 15:40 | 18 |
| 19 | 16:00 | 16:20 | 20 |
| 21 | 16:40 | 17:00 | 22 |
| 23 | 17:20 | 17:40 | 24 |
| 25 | 18:00 | 18:20 | 26 |
| 27 | 18:40 | 19:00 | 28 |
| 29 | 19:20 | 19:40 | 30 |
| 31 | 20:00 | 20:20 | 32 |
| 33 | 20:40 | 21:00 | 34 |

Bacteriological Evaluation

Five rats per treatment were swabbed on day 58. The swab suspensions were either plated on Petri dishes for CFU (colony forming units) counts or immobilized on glass slides for immunofluorescence for TCN (total cells number) counts.

Procedure for CFU Determination

Swab rats' teeth with a sterile cotton-tipped stick and place it immediately in 5 ml of sterile NaCl 0.9%

Vortex for 1 min and sonicate for 5 s at 50 W

Spirally plate the properly diluted suspensions on CBA, MS and HJL agar

Incubate CBA and MS plates at 37° C. and HJL plates at 45° C.

Procedure for TCN Determination

Put 10 μl of the undiluted swab suspension prepared for CFU determination per well on a 24 wells glass slide (Dynatech Produkte AG, Embrach Embraport, Switzerland), and air dry Fix by soaking in methanol for 2 min and air dry Incubate with 10 μl of the proper antibody or serum diluted in ELISA buffer (section 4.2.2.5) and incubate at 37° C. for 30 min Aspirate each drop from the side of the well and wash by soaking the slide first in ELISA buffer and then in distilled water. Air dry Apply 10 μl of goat-anti-rabbit IgG (H+L)–FITC (Sigma) diluted 1:400 and incubate at 37° C. for 30 min Wash as before and air dry Apply 49 μl of mounting fluid (section 4.2.2.5), cover with a glass slip and count the fluorescent cells with a fluorescence microscope.

Statistics

Data were treated with two-way ANOVA ((Snedecor and Cochran, 1980)).

RESULTS from the continuous association of the dairy strains by the way of a chilled dairy product feeding.

Bacteriological Evaluation (Table 14)

Colonization of the strain. 1.7 (+/−1.1)×$10^7$ CFU were counted for the plaque forming *A. viscosus* OMZ105, when the dairy product was supplemented with the non-adherent *S. thermophilus* control (NCC1536). The dairy strains could not be counted by microbiological methods. By immunofluorescence, however, a qualitative evaluation was tempted. The three adherent dairy strains could be recognized in the plaque samples from treatments 2 and 3. Since they were co-aggregated with other oral bacteria and mouth debris, thus generating big clusters, a precise quantification was impossible.

Variations in the total flora (TF). The three treatments containing the adherent tested strains *S. thermophilus* NCC1561 and *L. lactis* NCC2211 displayed significant reduced numbers of colony forming units on CBA compared with the control group containing the non-adherent strain *S. thermophilus* NCC 1536 (Table 14). Treatment 2 reduced the CFU counts with a significant factor of $P_F<0.01$ and treatment 3 even more significantly ($P_F<0.001$).

Modulation of *A. viscosus* OMZ105 tooth colonization by the tested strains. In the case of the plaque forming bacterium *A. viscosus* OMZ105, an apparently less pronounced but more significant decrease in the number of colony forming units was observed for the three treatments containing the tested adherent strains with respect to treatment 1 ($P_F<0.01$) (Table 14). By contrast the percentages of *A. viscosus* on the total CFU counts were not significantly different. Approximately 50% of the total CFU for all four treatments were identified as *A. viscosus* colonies.

TABLE 14

Mean values per rat of colony forming units for the total flora (TF) and
*A. viscosus* OMZ105 and their respective percentages (N = 5).

| Treatment | TF on CBA × $10^6$ | OMZ105 On CBA × $10^6$ | % OMZ105 on CBA | TF on MS × $10^4$ |
|---|---|---|---|---|
| 1 (NCC1536) | 32.5 +/− 13.87 | 17.3 +/− 11.01 | 52.8 +/− 23.09 | 41.9 +/− 41 n.s. |
| 2 (NCC1561) | 17.6 +/− 6.57** | 8.0 +/− 1.96** | 47.2 +/− 9.37 n.s. | 5.6 +/− 3.8 n.s. |
| 3 (NCC2211) | 13.9 +/− 4.85*** | 5.8 +/− 2.07** | 43.4 +/− 18.16 n.s. | 1.7 +/− 1.11 n.s. |
| SEM | 2.99 | 2.17 | 5.65 | 10.33 |
| $P_F$ | 0.001 | 0.01 | n.s. | n.s. |
| LSD 0.05* | 9.21 | 6.69 | — | — |
| LSD 0.01** | 12.92 | 9.37 | — | — |
| LSD 0.001*** | 18.25 | — | — | — |

Treatments 2-3 were compared with treatment 1.
SEM = standard error of the mean;
n.s. = not significant.
CBA = Columbia Blood Agar;
MS = Mitis-salivarius agar.
OMZ105: *A. naeslundii* genospecies 2.

In this in vivo assay, the strains that were supplied daily, displayed clear inhibitory effect on the total microflora, whose CFU significantly diminished. This diminution can be explained by the growth antagonism of the dairy strains versus oral species. For instance in vitro, all of them, including the non S-HA adhering *S. thermophilus* NCC1536, can inhibit the growth of *A. viscosus* OMZ105. However, in vivo such an effect can only be displayed by the S-HA adhering strains, since it was detected in the treatments 2-4 compared to the first.

In particular, since the animals had been infected with *A. viscosus* OMZ105, the quantification of this plaque-forming organism was possible at the end of the experimental period, and the decrease of its CFU could be closely monitored.

The percentages of *A. viscosus* OMZ105 on the total CFU did not decrease in parallel, therefore one can deduce that the growth antagonism effect was also displayed versus other species, i.e. *Veillonellae*, and consequently it is a global effect that is observed.

Thus the strains CNCM I-1985 and CNCM-1986 are able to modulate the oral microbial ecology, significantly decreasing the colonization extent of *A. naeslundii* genospecies 2, with which the rats had been infected.

Example 12

Production and Initial Analysis of Surfactant Substances from *S. thermophilus* NCC1561 and *S. thermophilus* NCC1536

*S. thermophilus* NCC1561 and *S. thermophilus* NCC1536 were grown overnight in 1 l of Belliker at 42° C. For biosurfactant production, the procedure described in Busscher et al. (1997) *Appl. Environ. Microbiol.* 63, 3810-3817, (Busscher et al., 1997) was used.

Preparation of the Surfactant Substances

Procedure

Wash cells three times in PBS

Resuspend in 200 ml of distilled water or PBS

Produce the biosurfactant by gently stirring the suspension for 2 or 4 h at room temperature Separate bacteria by centrifugation at 10000 rpm for 10 min Centrifuge supernatant twice at 10000 rpm for 10 min Freeze-dry and weigh both the pellet and the surfactant substances solutions.

The crude biosurfactant suspension was first analyzed by SDS-PAGE and then submitted to surface tension measurements.

Procedure for SDS-PAGE

SDS-PAGE was carried out with a precast 12.5% ExcelGel (Amersham Pharmacia Biotech). Silver staining was performed with the Plusone Silver Staining Kit (Amersham Pharmacia Biotech).

Procedure for Surface Tension Measurement

The surface tension of the biosurfactant suspensions was measured with a TVT1 Drop Volume Tensiometer (Lauda, Lauda-Königshofen, Germany), which is based on the drop volume principle. Briefly, the method consists in the exact determination of the volume of a suspension drop that detaches from a capillary. This volume (critical volume) is proportional to the surface tension ($\sigma$), whose value is calculated with the relation:

$$\sigma = V g \Delta \rho F / 2\pi r_{cap}$$

where:

$\sigma$ is the interfacial tension

V is the drop volume

G is the acceleration constant $\Delta\rho$ is the difference of the densities of both adjacent phases F is the correction factor $r_{cap}$ is the radius of the capillary The measurements were done in duplicate at 37° C. against air. Each measurement consisted of 10 cycles. A solution of 6 mg/ml of crude product released, made the water surface tension decrease from 70 to 51 mN/m (Table 15). SDS-PAGE profile of the bacteria released products, showed that there were many different substances of proteinaceous nature in the solution.

TABLE 15

Surface tension values of the biosurfactant suspensions compared to water and PBS. The values are the mean of two experiments, each one consisting of ten measurements.

|  | Crude extract concentration | Surface tension (mN/m) |
|---|---|---|
| Water | — | 69.07 +/− 0.01 |
| PBS | — | 68.13 +/− 0.30 |
| S. thermophilus NCC1561 | 6 mg/ml | 51.47 +/− 0.17 |
| S. thermophilus NCC1536 | 6 mg/ml | 51.67 +/− 1.32 |

Result

S. thermophilus NCC1561 and S. thermophilus NCC1536 cells are able to release substances with a surfactant activity. It is therefore possible that the biosurfactant produced by S. thermophilus NCC1561 makes the bacterium itself and the other oral strains established close to it detach from the tooth surface. By contrast, this action would not be displayed by S. thermophilus NCC1536, since this strain does not adhere to the teeth.

Example 13

Toothpaste

Toothpaste is prepared by adding $10^5$ cfu/ml of at least one of the lactic bacteria strain CNCM I-1984, CNCM I-1985, CNCM I-1986, CNCM I-1987 in a lyophilized form, to the following mixture containing: 1.65% Cetyl pyridinium chloride, 33.0% Sorbitol (70% soln), 25.0% Glycerin, 2.0% Sodium carboxymethyl cellulose, 0.25% Sodium fluoride, 26.3% Silica (RP 93), 8.1% Thickening Silica (Sident 22), 0.5% Sodium saccharine, 3.2% Poloxamer (Pluronic F108).

This toothpaste is intended for the prophylaxis or the treatment of root caries, dental plaque and other infections induced by A.naeslundii species.

Example 14

Yoghurt

5 L MRS culture medium are sterilized for 15 min at 121° C. and then inoculated with 5% by volume of an active culture of at least one of the S. thermophilus strain CNCM I-1984, CNCM I-1985 containing approximately $10^9$ cfu/ml. After incubation for 8 h at 41° C., a starter containing 4.5·$10^8$ cfu/ml is obtained.

5 L reconstituted skimmed milk having a dry matter content of 10%, to which 0.1% yeast extract has been added, are sterilized for 15 min at 121° C. and inoculated with 2% of an active culture of commercial thickening Streptococcus thermophilus containing approximately $10^9$ cells/ml. After incubation for 4 h at 41° C., a starter containing 4.5·$10^8$ cells/ml is obtained.

One batch of whole milk containing 3.7% fats strengthened with 2.5% skimmed milk powder and then pasteurized for 30 min at 90° C. is then inoculated with 2% by volume of the starter of at least one of the strains CNCM I-1984, CNCM I-1985 and 3% by volume of the starter of thickening Streptococcus thermophilus. The inoculated milk is stirred, poured into pots and incubated for 4 h at 41° C.

The yogurt obtained has a good firm and smooth texture and is intended for the health of the mouth.

Example 15

Chewing Gum

A chewing gum for preventing or treating root caries, dental plaque, or other A.naeslundii-related diseases can be prepared adding an active culture of at least one of the S. thermophilus strain CNCM I-1984, CNCM I-1985, so that it contains approximately $10^4$ to $10^9$ cfu/g, to the following typical ingredients: 67.5% Xylitol, 20% Gum base, 5% Calcium carbonate, 3% Glycerin, 2% Pluronic F127, 1% Cellulose gum, 0.5% Balast compounds and 1% Flavor.

Example 16

Pet Food Composition

A pet food for mouth health is obtained by preparing a feed mixture made up of corn, corn gluten, chicken and fish meal, salts, vitamins and minerals. The feed mixture is fed into a preconditioner and moistened. The moistened feed leaving the preconditioner is then fed into an extruder-cooker and gelatinized. The gelatinized matrix leaving the extruder is forced through a die and extruded. The extrudate is cut into pieces suitable for feeding to dogs, dried at about 110° C. for about 20 minutes and cooled to form pellets that have a water activity of about 0.6.

The pellets are sprayed with 3 coating mixtures. Each coating mixture contains active culture of at least one of the S. thermophilus strains CNCM I-1984, CNCM I-1985 but one coating mixture uses hydrogenated soy fat as a coating substrate, one coating mixture uses water as a coating substrate and one coating mixture uses protein digest as a coating substrate. The pellets contain approximately $10^4$ to $10^9$ cfu/g of said strains.

What is claimed is:

1. A composition for maintaining mammal mouth health by reducing *Actinomyces naeslundii* colonization therein, the composition comprising at least one biologically pure lactic bacteria strain selected from the group consisting of the biologically pure strains CNCM I-1984, CNCM I-1985, CNCM I-1986, and CNCM I-1987, wherein the strain is exogenous to oral microflora, said strain is selected for its ability to adhere to teeth pellicle and to produce an *Actinomyces naeslundii* growth inhibition factor, and which is present in an amount sufficient to reduce or inhibit the colonization of *Actinomyces naeslundii*, thus maintaining mouth health in a mammal that consumes the composition.

2. The composition according to claim 1, further comprising a bactenocin.

3. The composition according to claim 1, comprising at least $10^4$-$10^9$ cfu/g of the lactic bacteria strain.

4. A method of treating *Actinomyces naeslundii*-related diseases in mammals, which comprises administering to a mammal a composition according to claim 1.

5. The method according to claim 4, wherein the at least one bacteria strain is administered for reducing dental plaque or for treating root caries or infections.

6. The method according to claim 4, wherein the composition is administered by feeding it to the mammal.

7. A method of treating *Actinomyces naeslundii*-related diseases in mammals, the method comprising administering to a mammal at least one lactic bacteria strain selected from the group consisting of the strains CNCM I-1984, CNCM I-1985, CNCM I-1986, and CNCM I-1987, wherein the strain is selected for its ability to produce an *Actinomyces naeslundii* growth inhibition factor in an amount sufficient to reduce or inhibit the colonization of *Actinomyces naeslundii*, thus treating such diseases in a mammal that consumes the composition.

8. The method according to claim 7, wherein the at least one bacteria strain is administered for reducing dental plaque or for treating root caries or infections.

9. A dentifrice composition for maintaining mammal mouth health by reducing *Actinomyces naeslundii* colonization therein, the composition comprising at least one lactic bacteria strain selected from the group consisting of the strains CNCM I-1984, CNCM I-1985, CNCM I-1986, and CNCM I-1987, wherein the strain is exogenous to oral microflora, said strain is selected for its ability to adhere to teeth pellicle and to produce an *Actinomyces naeslundii* growth inhibition factor, and which is present in an amount sufficient to reduce or inhibit the colonization of *Actinomyces naeslundii*, thus maintaining mouth health in a mammal that consumes the composition.

10. A method of reducing dental plaque or of treating root caries or infections caused by *Actinomyces naeslundii* in mammals, the method comprising administering to a mammal in need of such treatment a lactic bacteria strain selected from the group consisting of the strains CNCM I-1984, CNCM I-1985, CNCM I-1986, and CNCM I-1987, wherein the strain is exogenous to the oral microflora, is selected for its ability to adhere to teeth pellicle and to produce an *Actinomyces naeslundii* growth inhibition factor, and is administered in an amount sufficient to reduce or inhibit the colonization of *Actinomyces naeslundii*, thus reducing dental plaque or treating root caries or infections in the mammal.

11. The method according to claim 10, wherein the lactic bacteria strain is of dairy origin.

12. The method according to claim 10, wherein the bacteria strain is administered to the mammal in an edible composition.

13. The method according to claim 12, wherein the edible composition contains at least $10^4$ to $10^9$ cfu/g of the lactic bacteria strain.

14. The method according to claim 10, wherein the lactic bacteria strain is administered in combination with a bacteriocin.

15. The method according to claim 10, wherein the mammal is a human.

16. The method according to claim 15, wherein the human is over 40 years old.

17. A method of making a composition that is effective for reducing dental plaque or of treating root caries or infections caused by *Actinomyces naeslundii* in mammals, the method comprising incorporating in an edible composition a lactic bacteria strain selected from the group consisting of the strains CNCM I-1984, CNCM I-1985, CNCM I-1986, and CNCM I-1987, wherein the strain is exogenous to the oral microflora, is selected for its ability to adhere to teeth pellicle and to produce an *Actinomyces naeslundii* growth inhibition factor, and is present in an amount sufficient to reduce or inhibit the colonization of *Actinomyces naeslundii*, thus reducing dental plaque or treating root caries or infections in a mammal that consumes the composition.

\* \* \* \* \*